US006379674B1

(12) United States Patent
Rabkin et al.

(10) Patent No.: US 6,379,674 B1
(45) Date of Patent: Apr. 30, 2002

(54) USE OF HERPES VECTORS FOR TUMOR THERAPY

(75) Inventors: Samuel D. Rabkin, Chevy Chase, MD (US); Masahiro Toda, Yokohama (JP); Robert L. Martuza, Chevy Chase, MD (US)

(73) Assignee: Georgetown University, Washington, DC (US)

( * ) Notice: Subject to any disclaimer, the term of this patent is extended or adjusted under 35 U.S.C. 154(b) by 0 days.

(21) Appl. No.: 09/064,174

(22) Filed: Apr. 22, 1998

Related U.S. Application Data

(60) Provisional application No. 60/055,142, filed on Aug. 12, 1997, now abandoned.

(51) Int. Cl.[7] .................. A61K 48/00; A61K 39/12; A61K 39/245; C12N 15/63
(52) U.S. Cl. ................ 424/199.1; 435/320.1; 435/235; 424/2.1; 424/93.2; 514/44
(58) Field of Search ............... 425/235, 320.1; 514/44; 424/199.1, 231

(56) References Cited

U.S. PATENT DOCUMENTS

| 5,571,515 A | 11/1996 | Scott et al. ............... 424/208.1 |
| 5,585,096 A | 12/1996 | Martuza et al. ............ 424/93.2 |

FOREIGN PATENT DOCUMENTS

| WO | 96/38741 | 12/1986 |
| WO | 96/00007 | 1/1996 |

OTHER PUBLICATIONS

Restifo et al. (1993) J. Immunother., vol. 14, 182–190.*
Huang et al. (1994) Science, vol. 264, 961–965.*
Andreansky et al. (1997) Canc. Res., vol. 57, 1502–1509.*
Miyatake et al. (1997) Canc. Gene. Ther., vol. 4 (4), 222–228.*
R. Martuza et. al., "G207: A Multiple Deletion Herpes Mutant for Brain Tumor", J. Neuro., vol. 82, No. 2, Feb. 1995, p. 377A.
M. Toda et al., "Intratumoral inoculation of a replication-–competent herpes simplex virus, G207, induces an antitumor immune response", Proc. Am. Assoc for C. Res., vol. 38, Mar. 1997, pp 175.
M.J. Davidson et al., "Determination of the Sequence Alteration in the DNA of the Herpes Simplex Virus Type 1 Temperature–sensitive Mutant ts K"; J. gen Virol. (1984), 65, 859–863.
C.L. Nastala et al., "Recombinant IL–12 Administration Induces Tumor Regression in Association with IFN–γ Production", J. Immun., vol. 153, Aug. 1994, pp. 1697–1706.
C. Tung et al., "Rapid Production of Interleukin–2 Secreting Tumor Cells by Herpes Simples Virus–Mediated Gene Transfer: Implications for . . . Production"; Human Gen. Therapy, 7:2217–2224, (1/96).

M. Toda et al., In Situ Cancer Vaccination: An IL–12 Defective Vector . . . Antitumor Activity, J. Immun., vol. 160, May 1998, pp. 4457–4464.
D'Angelica et al., "In vivo IL–2 Gene Transfection of Implanted Tumors with HSV vectors Induces a Systemic Antitumor Response," Immunobiology #3020, *Proceedings of the 87th Ann. Mtg. of the Am. Assoc. Cancer Res*, vol. 37, (Mar. 1996).
Toda et al., "Intratumoral Inoculation of a Replication–competent Herpes Simplex Virus, G207, Induces an Antitumor Immune Response," Pharmacology/Therapeutics (Preclinical and Clinical) #1176: *Proceedings of the 88th Ann. Mtg. of the Am. Assoc. Cancer Res*, vol. 38, (Mar. 1997).
R.G. Vile et al., "Targeted Gene Therapy for Cancer: Herpes Simplex Virus Thymidine Kinase Gene–mediated Cell Killing Leads to Anti–Tumour Immunity That Can Be Augmented By Co–expression of Cytokines in the Tumour Cells," *Biochemical Society Transactions*, vol. 25 (May 1997).
Richard G. Vile et al., Generation of an Anti–Tumour Immune Response in a Non–immunogenic Tumour: *J. Cancer* 71(2):267–74 (1997).
Wanli Bi et al., "An HSVtk–mediated Local and Distant Antitumor Bystander Effect in Tumors of Head and Neck Origin in Anthymic Mice," *Cancer Gene Therapy*, 4(4): 246–52 (1997).

(List continued on next page.)

*Primary Examiner*—Scott D. Prieber
*Assistant Examiner*—AnneMarie S. Beckerleg
(74) *Attorney, Agent, or Firm*—Foley & Lardner

(57) ABSTRACT

Eliciting a systemic antitumor immune response, in a patient who presents with or who is at risk of developing multiple metastatic tumors of a given cell type, entails, in one embodiment, inoculating a tumor in the patient with a pharmaceutical composition consisting essentially of (A) a herpes simplex virus (HSV) that infects tumor cells but that does not spread in normal cells and (B) a pharmaceutically acceptable vehicle for the virus, such that an immune response is induced that is specific for the tumor cell type and that kills cells of the inoculated tumor and of a non-inoculated tumor. In another embodiment, the pharmaceutical composition also comprises a defective HSV vector which contains an expressible nucleotide sequence encoding at least one immune modulator. In another embodiment, the pharmaceutical composition contains a second HSV that infects tumor cells but that does not spread in normal cells. According to the latter approach, both the first HSV and the second HSV may have genomes that comprise, respectively, an expressible nucleotide sequence coding for at least one immune modulator. In another embodiment, the pharmaceutical composition comprises, in addition to a herpes simplex virus (HSV) that infects tumor cells but that does not spread in normal cells, a viral vector comprising at least one expressible nucleotide sequence coding for at least one immune modulator.

8 Claims, 11 Drawing Sheets

OTHER PUBLICATIONS

S.J. Tapscott et al., "Gene Therapy of Rat 9L Gliosarcoma Tumors By Transduction With Selectable Genes Does Not Require Drug Selection," *Proc. Natl. Acad. Sci.,* 91: 8185–89 (Aug. 1994).

Sin–Ichi Miyatake et al., "Defective Herpes Simplex Virus Vectors Expressing Thymidine Kinase for the Treatment of Malignant Glioma," *Cancer Gene Therapy,* 4(4): 222–28 (1997).

Matthew J. During et al., "Long–Term Behavioral Recovery in Parkinsonian Rats by an HSV Vector Expressing Tyrosine Hydroxylase," *Science,* vol. 266, (Nov. 1994).

Peter A. Pechan et al., "A Novel 'Piggyback' Packaging System for Herpes Simplex Virus Amplicon Vectors," *Human Gene Therapy* 7:2003–13 (Oct. 1996).

Ann D. Kwong et al., "The Herpes Simplex Virus Amplicon," *Virology* 142: 421–25 (1985).

Pedro R. Lowenstein et al., "Herpes Simplex Virus (HSV–1) Helper Co–infection Affects the Distribution of an Amplicon Encoded Protein in Glia," *Molec. Neurosc.,* 5(13): 1625–30 (Aug. 1994).

Peyman Pakzaban, et al., "Effect of Exognous Nerve Growth Factor on Neurotoxicity of and Neuronal Gene Delivery by a Herpes Simplex Amplicon Vector in the Rat Brain," *Human Gene Therapy,* 5: 987–95 (Aug. 1994).

Howard M. Karpoff et al., "Prevention of Hepatic Tumor Metastases in Rats with Herpes Viral Vaccines and γ–Interferon," *J. Clin. Invest.* pp. 799–804 (Feb. 1997).

Cindy Tung et al., "Rapid Production of Interleukin–2–Secreting Tumor Cells by Herpes Simplex Virus–Mediated Gene Transfer: Implications for Autologous Vaccine Production," *Human Gene Therapy,* 7:2217–24 (Dec. 1996).

Alberto L. Epstein, "HSV–1 Amplicons. Advantages and Disadvantages of a Versatile Vector System," *Restorative Neurology and Neuroscience,* 8:41–43 (1995).

Alfred I. Geller et al., "An Efficient Deletion Mutant Packaging System for Defective Herpes Simplex Virus Vectors: Potential Applications to Human Gene Therapy and Neuronal Physiology," *Proc. Natl. Acad. Sci., USA,* 87: 8950–54 (Nov. 1990).

Richard R. Spaete et al., "The Herpes Simplex Virus Amplicon: A New Eucaryotic Defective–Virus Cloning–Amplifying Vector," *Cell,* 30:295–304 (Aug. 1982).

F. Lim et al., "Generation of High–Titer Defective HSV–1 Vectors Using an IE 2 Deletion Mutant and Quantitative Study of Expression in Cultured Cortical Cells," *BioTechniques,* 20(3):460–61 (Mar. 1996).

Giorgio Parmiani et al., "Cytokine Gene Transduction in the Immunotherapy of Cancer," *Adv. Pharmacol.,* 40:259–89 (1997).

J.C. Glorioso et al., "Development and Application of Herpes Simplex Virus Vectors for Human Gene Therapy," *Annu. Rev. Microbiol.* 49:675–710 (1995).

Alfred I. Geller, "Influence of the Helper Virus on Expression of β–Galactosidase from a Defective HSV–1 Vector, pHSVlac," *J. Virol. Methods,* 31:229–38 (1991).

Alfred I. Geller et al., "A Defective HSV–1 Vector Expresses *Eschirichia coli* β–Galactosidase in Cultured Peripheral Neurons," *Science,* 241:1667–69 (Sep. 1988).

Todo et al., "Treatment of Experimental Brain Tumors by Induction of Systemic Antitumor Immunity Using a Replication–Competent Herpes Simplex Virus", *The 88th Annual Meeting of American Association of Cancer Research* (San Diego, CA), Apr. 12–16, 1997.

Todo et al., Intraneoplastic Inoculation of a Replication–Competent Herpes Simplex Virus Induces Systemic Antitumor Immunity in Mice Bearing Syngeneic Neuroblastoma, Keystone Symposia: Molecular and Cellular Biology of Gene Therapy (Keystone, CO), Jan. 19–25, 1998.

Daniel L. Shawler et al., "Gene Therapy Appraches to Enhance Antitumor Immunity," *Adv. Pharmacol.,* 40:309–37 (1997).

* cited by examiner

USE OF HERPES VECTORS FOR TUMOR THERAPY

This application is a continuation of provisional U.S. Application No. 60/055,142, filed on Aug. 12, 1997, now abandoned.

BACKGROUND OF THE INVENTION

Induction of tumor-specific immunity is an attractive approach for cancer therapy because of the prospect of harnessing the body's own defense mechanisms, rather than using standard toxic therapeutic agents, to provide long-term protection against tumor existence, growth and recurrence. This strategy is attractive for its potential to destroy small metastatic tumors which may escape detection, and to provide immunity against recurrent tumors.

In principle, an immunotherapy would depend on the presence of tumor-specific antigens and on the ability to induce a cytotoxic immune response that recognizes tumor cells which present antigens. Cytotoxic T lymphocytes (CTL) recognize major histocompatibility complex (MHC) class I molecules complexed to peptides derived from cellular proteins presented on the cell surface, in combination with co-stimulatory molecules. Mueller et al., *Annu. Rev. Immunol.* 7: 445–80 (1989). In fact, tumor-specific antigens have been detected in a range of human tumors. Roth et al., *Adv. Immunol.* 57: 281–351 (1994); Boon et al., *Annu. Rev. Immunol.* 12: 337–65 (1994).

Some cancer vaccination strategies have focused on the use of killed tumor cells or lysates delivered in combination with adjuvants or cytokines. More recently, gene transfer of cytokines, MHC molecules, co-stimulatory molecules, or tumor antigens to tumor cells has been used to enhance the tumor cell's visibility to immune effector cells. Dranoff & Mulligan, *Adv. Immunol.* 58: 417–54 (1995).

The therapeutic use of "cancer vaccines" has presented major difficulties, however. In particular, conventional approaches require obtaining and culturing a patient's autologous tumor cells for manipulation in vitro, irradiation and subsequent vaccination, or the identification and purification of a specific tumor antigen.

SUMMARY OF THE INVENTION

It is therefore an object of the present invention to provide a method of eliciting a systemic antitumor immune response in a patient who presents with or who is at risk of developing multiple metastatic tumors without manipulating the patient's autologous tumor cells or identifying or purifying specific antigens.

It is also an object of the present invention to provide vectors for effecting this method.

In accomplishing these and other objectives, the present invention provides a method of eliciting a systemic antitumor immune response in a patient who presents with or who is at risk of developing multiple metastatic tumors of a given cell type. In accordance with one aspect of the invention, the method comprises inoculating a tumor in the patient with a pharmaceutical composition consisting essentially of:
  (A) a herpes simplex virus (HSV) that infects tumor cells but that does not spread in normal cells, and
  (B) a pharmaceutically acceptable vehicle for the virus, such that an immune response is induced that is specific for the tumor cell type and that kills cells of the inoculated tumor and of a non-inoculated tumor. In accordance with one embodiment, the virus replicates in dividing cells and exhibits attenuated replication in non-dividing cells. In accordance with another embodiment, the virus is replication-defective. In accordance with yet another embodiment, the virus is conditionally replication-competent. In accordance with another embodiment, the virus is of a vaccine strain. In accordance with one embodiment, the genome of the virus comprises at least one expressible nucleotide sequence coding for at least one immune modulator.

In accordance with another aspect of the invention, the method comprises inoculating a tumor in the patient with a pharmaceutical composition comprising:
  (A) a herpes simplex virus that infects tumor cells but that does not spread in normal cells, and whose immunological properties consist essentially of inducing an immune response that is specific for the tumor cell type and that kills cells of the inoculated tumor and of a non-inoculated tumor,
  (B) a defective herpes simplex virus vector containing at least one expressible nucleotide sequence encoding at least one immune modulator, and
  (C) a pharmaceutically acceptable vehicle for the virus and defective vector, such that an immune response is induced that is specific for the tumor cell type and that kills cells of the inoculated tumor and of a non-inoculated tumor.

In accordance with another aspect of the invention, the method comprises inoculating a tumor in the patient with a pharmaceutical composition comprising:
  (A) a first herpes simplex virus (HSV) that infects tumor cells but that does not spread in normal cells, and whose immunological properties consist essentially of inducing an immune response that is specific for the tumor cell type and that kills cells of the inoculated tumor and of a non-inoculated tumor,
  (B) a second herpes simplex virus (HSV) that infects tumor cells but that does not spread in normal cells, and
  (C) a pharmaceutically acceptable vehicle for the viruses, such that an immune response is induced that is specific for the tumor cell type and that kills cells of the inoculated tumor and of a non-inoculated tumor.

In accordance with another aspect of the present invention, the method comprises inoculating a tumor in the patient with a pharmaceutical composition comprising:
  (A) a first herpes simplex virus (HSV) that infects tumor cells but that does not spread in normal cells, wherein the genome of the first herpes simplex virus comprises at least one expressible nucleotide sequence coding for at least one immune modulator,
  (B) a second herpes simplex virus (HSV) that infects tumor cells but that does not spread in normal cells, wherein the genome of the second herpes simplex virus comprises at least one expressible nucleotide sequence coding for at least one immune modulator, and
  (C) a pharmaceutically acceptable vehicle for the viruses, such that an immune response is induced that is specific for the tumor cell type and that kills cells of the inoculated tumor and of a non-inoculated tumor.

In accordance with another aspect of the present invention, the method comprises inoculating a tumor in the patient with a pharmaceutical composition comprising:
  (A) a herpes simplex virus (HSV) that infects tumor cells but that does not spread in normal cells,
  (B) a viral vector comprising at least one expressible nucleotide sequences coding for at least one immune modulator, and (C) a pharmaceutically acceptable vehicle for the virus and viral vector, such that an immune response is induced that is specific for the tumor cell type and that kills cells of the inoculated tumor and of a non-inoculated tumor. The viral vector may be, for example, an adenoviral vector, a adenovirus-associated vector, a retroviral vector, or a vaccinia virus vector.

Mutated viruses useful in the methods of the invention also are provided. In accordance with one aspect of the invention, there is provided a herpes simplex virus that is incapable of expressing both (i) a functional γ34.5 gene product and (ii) a ribonucleotide reductase, wherein the genome of the virus comprises at least one expressible nucleotide sequence encoding at least one immune modulator. In accordance with another aspect of the invention, there is provided a herpes simplex virus ICP4 mutant tsK, the genome of which has been altered to incorporate at least one expressible nucleotide sequence coding for at least one immune modulator.

Compositions for effecting the methods of the present invention also are provided. In accordance with one aspect of the invention, a composition for eliciting a systemic antitumor immune response in a patient who presents with or who is at risk of developing multiple metastatic tumors of a given cell type comprises:

(A) a herpes simplex virus that is incapable of expressing both (i) a functional γ34.5 gene product and (ii) a ribonucleotide reductase, and (B) a defective herpes simplex virus vector containing at least one expressible nucleotide sequence encoding at least one immune modulator.

In accordance with another aspect of the invention, a composition for eliciting a systemic antitumor immune response in a patient who presents with or who is at risk of developing multiple metastatic tumors of a given cell type comprises:

(A) a herpes simplex virus that is replication-defective, and whose immunological properties consist essentially of inducing an immune response that is specific for the tumor cell type and that kills cells of the inoculated tumor and of a non-inoculated tumor, and (B) a defective herpes simplex virus vector containing at least one expressible nucleotide sequence encoding at least one immune modulator.

In accordance with yet another aspect of the invention, a composition for eliciting a systemic antitumor immune response in a patient who presents with or who is at risk of developing multiple metastatic tumors of a given cell type comprises:

(A) a herpes simplex virus that is conditionally replication-competent, and (B) a defective herpes simplex virus vector containing at least one expressible nucleotide sequence encoding at least one immune modulator.

These and other objects and aspects of the invention will become apparent to the skilled artisan in view of the teachings contained herein.

DETAILED DESCRIPTION OF THE PREFERRED EMBODIMENTS

Figure 1A:
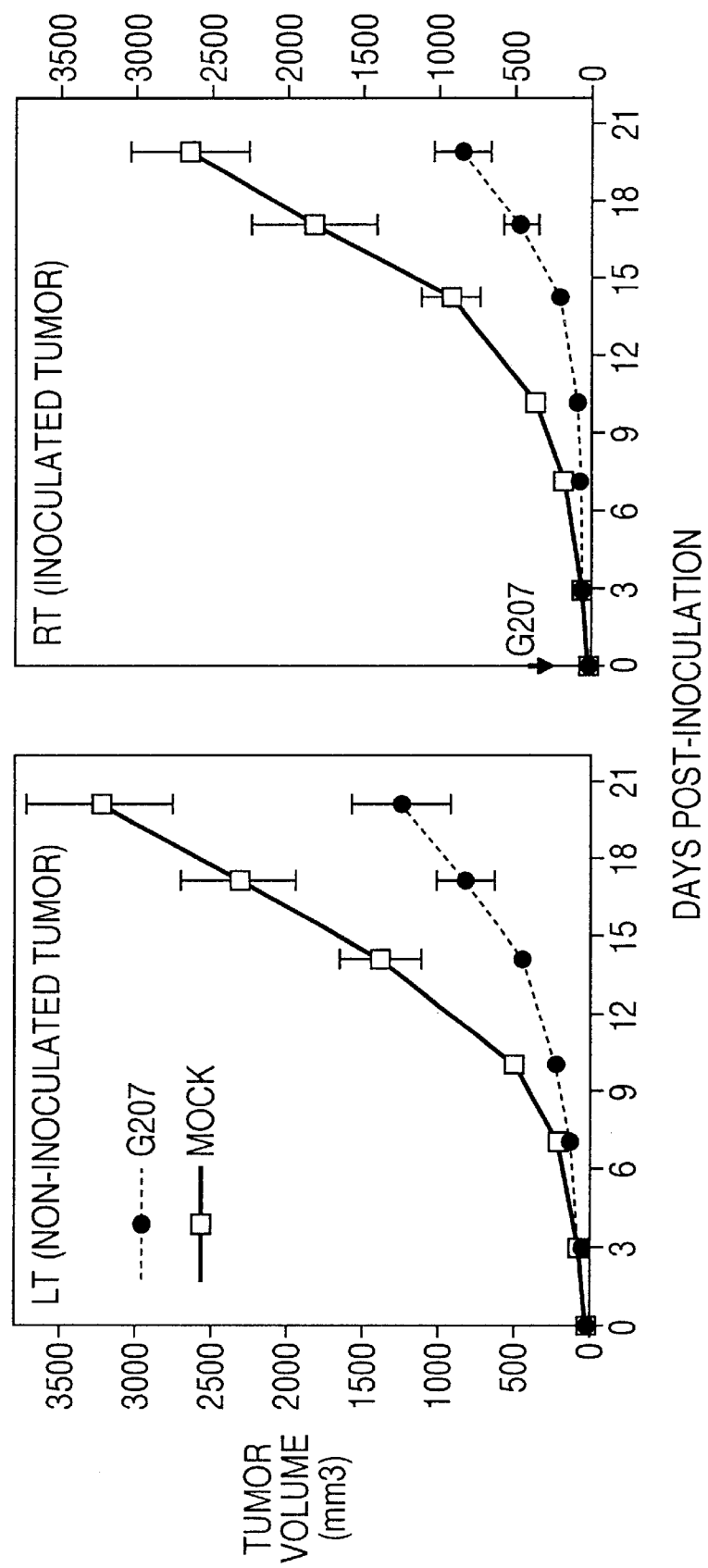
FIG. 1A shows that intratumoral inoculation of CT26 tumors in BALB/c mice with G207 inhibits growth of the inoculated tumor (rt) and of a non-inoculated tumor at a distant site (lt). Bars represent means±SEM of 6 mice per group. Tumor Volume=(width×length×height).

A new and improved approach for eliciting a systemic immune response in patients presenting with multiple metastatic tumors has been developed. In accordance with these developments, the present invention provides a method of eliciting a systemic antitumor immune response in a patient presenting with, or at risk of developing, multiple metastatic tumors by inoculating at least one tumor with a mutated herpes simplex virus (HSV). The inoculation invokes a highly specific antitumor immune response which kills cells of the inoculated tumor, as well as cells of distant, established, non-inoculated tumors.

The ability to treat patients presenting with multiple metastatic tumors represents a significant advantage over conventional approaches which focus on the treatment of a single tumor mass. The efficacy of conventional cytotoxic viral vector-based approaches depends on the viral infection of all tumor cells in the patient. It is extremely difficult to obtain broad or systemic distribution of viral vectors in vivo, however, and therefore difficult to infect all tumor cells of a localized solid tumor, and virtually impossible to infect all tumor cells in a patient presenting with multiple metastatic tumors. The method of the present invention, which does not require the targeting of a viral vector to every tumor cell, therefore offers a distinct improvement over these methods. Moreover, with recent improvements in cancer therapy of primary tumors, many patients survive longer and are at risk of developing multiple metastatic tumors. Accordingly, the ability to treat these patients effectively represents a needed improvement in cancer therapy.

The viruses used in accordance with the present invention are mutated herpes simplex viruses that infect tumor cells but do not spread efficiently to or replicate efficiently in normal cells or tissue, thereby causing no disease or pathology in and of itself. For example, a virus that replicates in dividing cells and exhibits attenuated replication in non-dividing cells is useful in accordance with the present invention, as is a virus that is replication-defective. The virus may be of type 1 (HSV-1) or type 2 (HSV-2). Various HSV-1 mutants have been used for local cytotoxic tumor therapy to destroy tumor cells in situ, yet spare normal tissue. Mineta et al., *Nature Medicine* 1: 938–43 (1995); Martuza et al., *Science* 252: 854–56 (1991); Boviatsis et al., *Gene Therapy* 1: 323–331 (1994); Randazzo et al., *Virology* 211: 94–101 (1995); Andreansky et al., *Proc. Natl. Acad. Sci. USA* 93: 11313–18 (1996). Any of these mutants can be used in accordance with the present invention, as can vaccine strains of HSV. A number of anti-viral drugs (i.e., acyclovir and foscarnet) against herpes simplex virus are available that would allow unforeseen viral spread to be treated.

In a preferred embodiment of the present invention, the virus replicates in dividing cells and exhibits attenuated replication in non-dividing cells. For instance, U.S. Pat. No. 5,585,096 describes a suitable virus, illustrated by strain G207, which is incapable of expressing both (i) a functional γ34.5 gene product and (ii) a ribonucleotide reductase. (The contents of U.S. Pat. No. 5,585,096 are incorporated herein by reference.) G207 replicates in dividing cells, effecting a lytic infection with consequent cell death, but is highly attenuated in non-dividing cells, thereby targeting viral spread to tumors. G207 is non-neuropathogenic, causing no detectable disease in mice and non-human primates. Mineta et al., *Nature Medicine* 1: 938–43 (1995).

Pursuant to another aspect of the present invention, the virus is replication-defective. Exemplary of such a virus is tsK, a temperature-sensitive herpes simplex virus mutant in ICP4. Davison et al., *J. Gen. Virol.* 65: 859–63 (1984). The ability of tsK to replicate is temperature-dependent, with 31.5° C. permissive for replication, and 39.5° C. nonpermissive. tsK can replicate with varying ability between these temperatures. Because body temperature is about 39.5° C., tsK is expected to be replication-defective in vivo. This has been confirmed by in vivo experiments with tsK in rats.

In accordance with another aspect of the present invention, the virus is conditionally replication-competent. An example of such a virus is G92A, whose ability to replicate is cell-type dependent. G92A is described in more detail in U.S. application Ser. No. 08/486,147, filed Jun. 7, 1995, the contents of which are incorporated herein by reference.

In one embodiment of the invention, the immunological properties of the mutated herpes simplex virus consist essentially of inducing an immune response that is specific for the tumor cell type and that kills cells of the inoculated tumor and of a non-inoculated tumor. As used above, the phrase "consisting essentially of" excludes another feature that would affect significantly a material aspect of the invention. For example, in accordance with this embodiment, the genome of the mutated virus does not comprise an expressible immune modulator, such as IL-2. As discussed below, other embodiments of the invention encompass mutant viruses whose genomes do comprise an expressible immune modulator.

Another embodiment of the present invention relates to a composition, consisting essentially of the herpes simplex virus and a pharmaceutically acceptable carrier, that is administered to a patient who suffers from or who is at risk of developing multiple, metastatic tumors. The composition is administered directly to the tumors cells in situ. In this description, the phrase "consisting essentially of" excludes a step or other feature that would affect significantly a material aspect of the invention. Thus qualified, a composition of this embodiment would include, for example, the prescribed herpes simplex virus with no other virus or defective virus vector; this, because an additional virus would substantially complicate the inventive protocol. The invention also encompasses the administration of this composition in combination with another therapy, such as chemotherapy or radiation treatment.

In accordance with another embodiment, more than one mutated herpes simplex virus is administered. This embodiment can be effected by administering a single composition comprising more than one mutated herpes simplex virus and a pharmaceutically acceptable vehicle for the viruses, or by administering more than one composition, each composition comprising at least one mutated herpes simplex virus and a pharmaceutically acceptable vehicle for the virus or viruses. In one embodiment, a composition is administered that comprises (A) a first mutated herpes simplex virus, (B) a second mutated herpes simplex virus and (C) a pharmaceutically acceptable carrier for the viruses. In an another embodiment, a composition is administered that consists essentially of (A) a first mutated herpes simplex virus, (B) a second mutated herpes simplex virus and (C) a pharmaceutically acceptable carrier for the viruses. As set forth above, the phrase "consisting essentially of" excludes a step or other feature that would affect significantly a material aspect of the invention. Thus, this embodiment would entail, for example, the administration of the prescribed first and second herpes simplex viruses with no other virus or defective virus vector.

The inoculation of a tumor with one or more mutated herpes simplex viruses in accordance with the present invention induces a systemic tumor-specific immune response that is specific for the cell type of the inoculated tumor and that kills cells of the inoculated tumor and of other, non-inoculated tumors. The induced cell death is observed, for example, as inhibited tumor growth or as reduced tumor size. In the examples set forth below, the induced cell death is observed as an inhibition of the growth of the inoculated tumor and of distant, established, non-inoculated tumors. In some instances, the tumors shrink to undetectable sizes. In one of the murine models studied, CT26, the immune response is correlated with cytotoxic T lymphocytes (CD8$^+$) that recognize a major histocompatibility complex (MHC) class I-restricted peptide that is a dominant tumor antigen.

As discussed above, the composition is administered directly to tumor cells of the patient, in situ. This can be accomplished by procedures known in the art, for example, by intratumoral inoculation during surgery, such as surgery for debulking a tumor, into external melanomas, or stereotactically into the tumor bed. Other approaches for targeting tumors also are appropriate. Generally, the maximum safe dose is administered at weekly intervals if the tumor is readily accessible, or is administered during surgery or tumor biopsy.

The pharmaceutically acceptable vehicle for the virus can be selected from known pharmaceutically acceptable vehicles, and should be one in which the virus is stable. For example, it can be a diluent, solvent, buffer, and/or preservative. An example of a pharmaceutically acceptable vehicle is phosphate buffer containing NaCl. Other pharmaceutically acceptable vehicles aqueous solutions, non-toxic excipients, including salts, preservatives, buffers and the like are described in REMINGTON'S PHARMACEUTICAL SCIENCES, 15th Ed. Easton: Mack Publishing Co. pp 1405–1412 and 1461–1487 (1975) and THE NATIONAL FORMULARY XIV., 14th Ed. Washington: American Pharmaceutical Association (1975), the contents of which are hereby incorporated by reference.

The HSV may been introduced into animals by intratumor, intravenous, intraperitoneal, intramuscular, intratracheal, intravesicle, intraintestinal, intrarectal, intraoral, intraocular or intraarterial injections. For introduction into the bladder, the HSV can be instilled into the bladder by intravesicle infusion. For introduction into the rectum, the HSV can be instilled using a local enema. For introduction into the lung, the HSV can be introduced by instillation through a tube, infusion, inhalation into the trachea or injection into the trachea.

Huang et al., *Science* 264: 961–65 (1994), demonstrated that the priming of an immune response against a MHC class I-restricted tumor antigen involves the transfer of that antigen to host bone marrow-derived antigen-presenting cells (APCs) prior to its presentation to $CD8^+$ T cells. While not wanting to be bound by any theory, the present inventors believe that local HSV infection of a tumor might induce circulating precursors to differentiate into APCs. A subset of macrophages are able to present exogenous antigens on MHC class I molecules to $CD8^+$ T cell clones. Rock et al., *J. Immunol.* 150: 438–46 (1993). The lytic destruction or virally-induced death of tumor cells might release tumor antigens which are picked up by APCs and carried to the draining lymph nodes. There they would be processed and presented to $CD8^+$ T cells. Associative recognition of HSV-specific and tumor-specific antigens might also play a role in the strength of the response. Tumor cells infected with replication-competent HSV would have maturing virions budding from their cell membranes and may also process viral antigens for MHC class-I presentation likes APCs do. The HSV-infected tumor cells therefore might induce T cell-mediated immune reactions directly. Some of the immune response induced by co-presentation of viral and tumor antigens may be triggered thereafter by only one of the co-expressed antigens.

In another preferred embodiment, one or more immune modulators are delivered to the tumor cells in addition to the mutated herpes simplex virus described above. Examples of immune modulators useful in the present invention include cytokines, co-stimulatory molecules, and chemokines. Delivery of one or more immune modulators can be effected, for example, by means of a mutated herpes simplex virus that comprises one or more expressible nucleotide sequences encoding one or more cytokines or other immune-modulatory genes, or by means of more than one mutated herpes simplex virus, each of which comprises one or more expressible nucleotide sequences encoding one or more cytokines or other immune-modulatory genes. Non-herpes simplex virus vectors also can be used to effect delivery of one or more immune modulators. For example, one or more adenoviral vectors, adenovirus-associated vectors, retroviral vectors, or vaccinia virus vectors comprising one or more expressible nucleotide sequences encoding one or more immune-modulatory genes can be used in accordance with this embodiment. See, e.g., Shawler et al., *Adv. Pharacol.* 40: 309–37 (1997), discussing gene transfer of immunostimulatory cytokines.

The present invention also comprehends a situation where the patient receives both a mutated herpes simplex virus and a defective herpes simplex virus vector which contains the genes for one or more immune modulators, and where the former virus acts as a helper virus for the defective vector. Additionally, the invention encompasses the administration of one or more mutated herpes simplex viruses and more than one defective herpes simplex virus vectors, where each defective vector contains the genes for one or more immune modulators, and where the former virus or viruses act as helpers for the defective vectors. Where one or more helper viruses are administered, the immunological properties of the helper viruses, i.e., the mutated herpes simplex viruses, consist essentially of inducing an immune response that is specific for the tumor cell type and that kills cells of the inoculated tumor and of a non-inoculated tumor. Thus employed, "consisting essentially of" excludes another feature that would affect significantly a material aspect of the invention. Accordingly, the use of this phrase excludes, for example, the administration of a helper virus vector that is capable of expressing an immune modulator, such as IL-2.

Examples of immune modulators that are useful in accordance with the present invention include IL-1, IL-2, IL-3, IL-4, IL-6, IL-7, IL-12, G-CSF, GM-CSF, IFN-α, IFN-γ, TNF-α and B7. See, e.g., Parmiani et al., *Adv. Pharmacol.* 40: 259–89 (1997); Shawler et al., *Adv. Pharmacol.* 40: 309 (1997). For convenience, the use of IL-12 is exemplified in the discussion which follows. It is to be understood, however, that other immune modulators can be used in its place or in addition thereto. Also, where the present description refers to "an immune modulator," it is to be understood that the invention encompasses one or more immune modulators.

The cytokine IL-12 is a heterodimeric cytokine, composed of 35 kD (p35) and 40 kD (p40) subunits, that binds to receptors present on NK and T cells. The high-affinity receptor is composed of two β-type cytokine receptor subunits that individually behave as low affinity receptors. IL-12 plays a multi-functional role in the immune system, augmenting the proliferation and cytotoxic activity of T cells and NK cells, regulating IFN-γ production and promoting the development of $CD4^+$ T helper (Th1) cells.

The antitumor activity of IL-12 has been demonstrated in a number of different murine tumor models, both solid and metastatic, with systemic administration of recombinant IL-12, fibroblasts or tumor cells engineered to secrete IL-12, and viral vectors expressing IL-12. IL-12 immunotherapy is less effective with other tumor cell lines such as CT26, C26, MCH-1-A1, and TS/A. Zitvogel et al., *Eur. J. Immunol.* 26: 1335–41 (1996). Systemic delivery of rIL-12 has been shown to have potent antitumor effects in various animal models. Prolonged exposure to IL-12 can have deleterious side effects like those observed with many cytokines, however.

Transfer of immune modulatory genes directly to the tumor cells is advantageous because the genes are expressed within the tumor at the site of their action in concert with putative tumor antigens. In accordance with the present invention, therefore, tumors are modified in situ to make tumor cells a source of immune modulator production.

Defective herpes simplex virus vectors are plasmid-based vectors which are unable to replicate on their own because they lack viral genes, but which contain specific HSV sequences that, in the presence of helper herpes simplex virus, support DNA replication and subsequent packaging into virus particles. Lim et al., *BioTechniques* 20(3): 460 (1996); Spaete and Frenkel, *Cell* 30: 295–304 (1982). In accordance with the present invention, the defective herpes simplex virus vector contains one or more nucleotide sequences encoding one or more cytokines or other immune modulators. Any herpes simplex virus described above can be used as helper virus, such as a replication-competent virus, a replication-defective virus, or a conditionally replication-competent virus. Because a viral genome length of DNA (~153 kb) is packaged, each defective vector can contain multiple copies of the immune modulator gene. For example, a defective vector containing an IL-12 gene can contain approximately 15 copies of the IL-12 gene (based on the size of the IL-12-containing plasmid), which can transduce both dividing and non-dividing cells at high efficiency. The viral DNA does not integrate into the infected cell genome, and with the CMV promoter driving IL-12 expression, expression is strong but transient. In accordance with one aspect of the present invention, a defective HSV vector is used to deliver one or more immune modulators such as IL-12 in combination with G207 as a helper virus. In accordance with another aspect of the present invention, a defective HSV vector is used to deliver one or more immune modulators such as IL-12 in combination with tsK as a helper virus. The construction of defective herpes virus vectors and their use with helper viruses is known in the art. For example, see Spaete & Frankel, supra, and Geller et al., *Proc. Nat'l Acad. Sci. USA* 87: 8950–54 (1990).

The defective IL-12-containing vector infects a number of different tumor cells which then produce and secrete IL-12 in vivo. Cells that are highly susceptible to HSV infection, but where the helper virus replicates poorly and therefore does not rapidly destroy the cells, may be the highest producers of IL-12 in vivo. The IL-12 acts as an adjuvant for the immune response elicited by the herpes simplex virus. In the murine models studied, the enhanced immune response is correlated with heightened induction of tumor-specific CTL activity and IFN-γ production by splenocytes, as described in more detail in the examples below.

The use of one or more defective herpes simplex virus vectors containing one or more immune modulators and one or more helper herpes simplex viruses in accordance with the present invention kills cells of the inoculated tumor and of other, non-inoculated tumors. This antitumor effect is significantly greater than that observed when a tumor is inoculated with a mutated herpes simplex virus alone, revealing a synergistic effect.

As discussed above, the immune response elicited in accordance with the present invention kills cells of the inoculated tumor and also kills non-inoculated tumor cells, including cells of distant, non-inoculated tumors. This effect makes this method particularly useful for treating patients presenting with multiple metastatic tumors of a given cell type. It also represents an improvement in the treatment of localized, non-metastatic tumors because the method kills tumor cells that are not directly targeted by the administered virus.

Any type of tumor can be treated in accordance with the present invention, including non-metastatic tumors, tumors with metastatic potential, and tumors already demonstrating an ability to metastasize. Examples of tumor cell types that can be treated in accordance with the present invention include astrocytoma, oligodendroglioma, meningioma, neurofibroma, glioblastoma, ependymoma, Schwannoma, neurofibrosarcoma, and medulloblastoma cell types. The invention also is useful in treating melanoma cells, pancreatic cancer cells, prostate carcinoma cells, head and neck cancer cells, breast cancer cells, lung cancer cells, colon cancer cells, lymphoma cells, hepatoma cells, ovarian cancer cells, renal cancer cells, neuroblastomas, squamous cell carcinomas, sarcomas, and mesothelioma and epidermoid carcinoma cells.

The embodiments of the invention are further illustrated through examples which show aspects of the invention in detail. These examples illustrate specific aspects of the invention and do not limit its scope.

EXAMPLES

Example 1
Antitumor Efficacy of G207 in CT26 Cell Line
The antitumor efficacy of G207 was evaluated in a bilateral, established subcutaneous tumor model with CT26 cells as described below.

Cell Line
The murine colorectal carcinoma CT26 cell line has been widely used as a syngeneic tumor model to study immunotherapy. Fearon et al. *Cancer Res.* 35: 2975–80 (1988); Wang, et al., *J Immunol.* 154: 4685–92 (1995); Huang et al., *Proc. Natl. Acad. Sci. USA* 93: 9730–35 (1996). CT26 is a transplantable colon epithelial tumor induced by intrarectal injections of N-nitroso-N-methylurethane in female BALB/c mice (H-$2^d$). Corbett et al., *Cancer Res.* 35: 2434–39 (1975).

In normal mice, CT26 is poorly immunogenic: $10^3$–$10^4$ cells can cause a lethal tumor and do not induce detectable tumor-specific CTL. Fearon et al., supra; Wang et al., supra. AH1, a nonmutated nonamer derived from the envelop protein (gp70) of an endogenous ecotropic murine leukemia provirus (MuLV), env-1, has been identified as the immunodominant MHC class I-restricted antigen for CT26. Huang et al., supra. Adoptive transfer of peptide-specific CTL lines has been able to cure established subcutaneous CT26 tumors, demonstrating the correlation between induction of tumor-specific CTL and an antitumor effect.

Herpes simplex virus does not grow in many rat cells, and attenuated viruses like G207 do not grow well in many mouse tumors either. This is in contrast to their excellent growth in most human tumor lines. However, studies in human tumor lines require the use of athymic mice. CT26 was chosen as a model cell line after several years of trying to find a good syngeneic system for studying the immune effects of attenuated conditionally replicated herpes vectors, such as G207.

Infection of CT26 Cells
Tumor cells ($1\times10^5$) were injected subcutaneously in the bilateral flanks of female BALB/c mice (National Cancer Institute (Rockville, Md.)). When subcutaneous tumors were palpably growing (approximately 5 mm in diameter), mice were unilaterally inoculated into the right side tumor with either G207 virus in 50 µl of virus buffer (150 mM NaCl, 20 mM Tris, pH 7.5) and modified Eagle's medium (MEM) (1:1), or with 50 µl of mock-infected extract ("mock"), prepared from mock-infected cells using the same procedures as those used for the virus inoculum. A second injection of the same composition was given 7 days later in some experiments. Tumor size was measured by external caliper. All animal procedures were approved by the Georgetown University Animal Care and Use Committee.

Figure 1B:
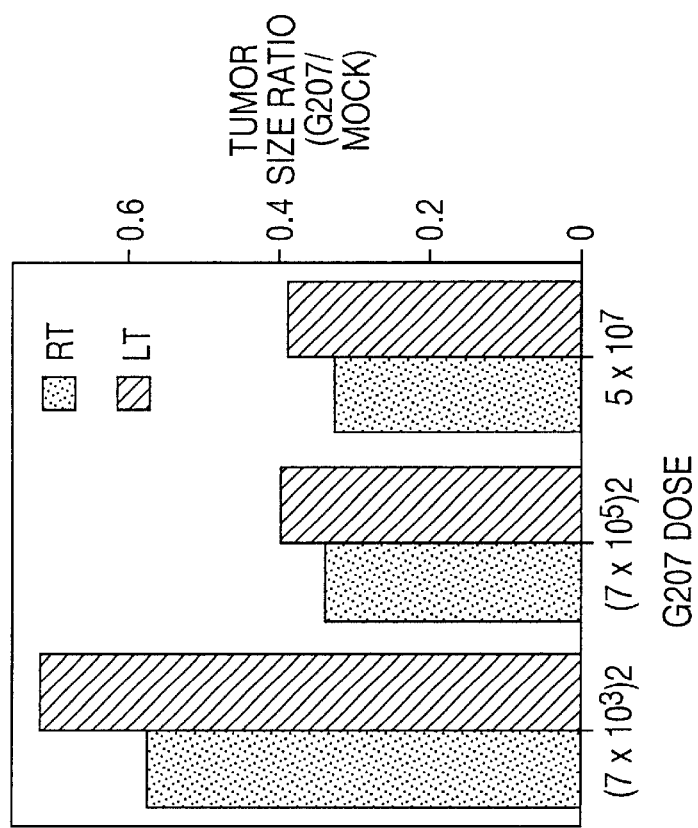
FIG. 1B shows that intradermal inoculation of CT26 tumors in BALB/c mice with G207 has no significant effect on tumor growth. Bars represent means±SEM of 6 mice per group. Tumor Volume=(width×length×height).
Figure 1C:
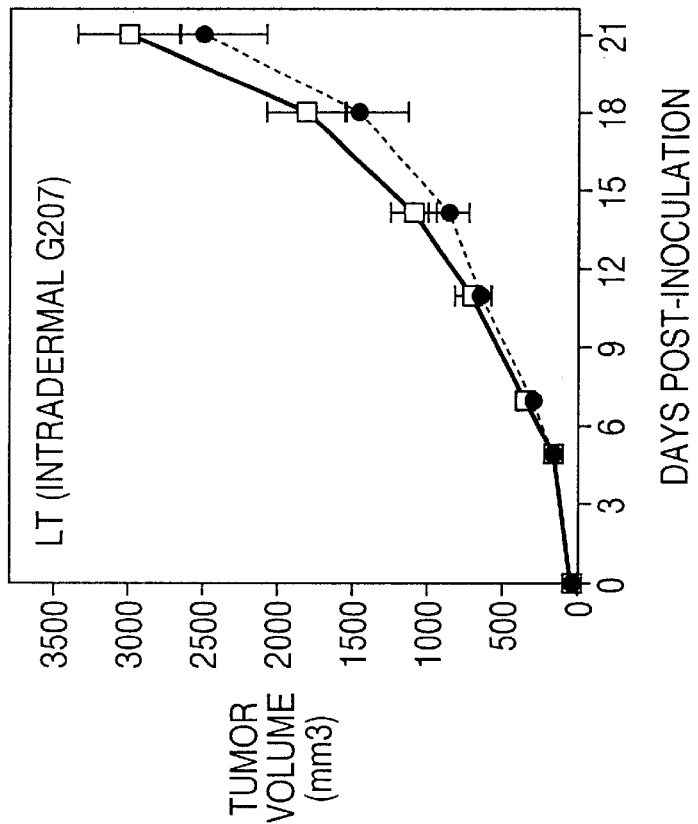
FIG. 1C shows that increasing the intratumoral dose of G207 results in decreased bilateral tumor growth of CT26 tumors in BALB/c mice. The bars show the average of 6 animals per group.

As shown in FIG. 1C, inoculation with G207 resulted in a reduction in tumor growth of both the inoculated tumors (Rt), as well as of their non-inoculated contralateral counterparts (Lt) when compared to mock-inoculated controls ($p<0.0005$ (Rt) and $p<0.001$ (Lt) on day 21 postinfection; unpaired t-test). At the time of the second inoculation, 7 days after the first inoculation, lacZ expression from G207 was detected by X-gal histochemistry in the inoculated tumor but not the non-inoculated tumor.

Two intratumoral inoculations with a lower dose of G207 ($7\times10^3$ plaqueforming units (pfu)) induced significant growth inhibition of the bilateral tumors compared to controls ($p<0.01$ (Rt) and $p<0.05$ (Lt) on day 21 postinfection; unpaired t-test), but to a lesser degree than the higher dose (see FIG. 1C).

A single unilateral intratumoral inoculation with $5\times10^7$ pfu of G207 caused a large reduction in bilateral tumor growth (FIG. 1A), comparable to the double inoculation with $7\times10^5$ pfu (FIG. 1C).

The antitumor effect on the non-inoculated contralateral tumor depended upon intratumoral inoculation of G207, as intradermal inoculation of G207 in the right flanks of mice with established unilateral tumors in the left flanks had no effect on tumor growth (see FIG. 1B).

Role of T Cells in Immune Response

To evaluate the potential role of T cells in the herpes simplex virus-induced inhibition of tumor growth according to the present invention, the antitumor efficacy of intratumoral G207 inoculation was tested in athymic mice. There was no effect of intratumoral inoculation of $7\times10^5$ pfu of G207. Higher dose G207 inoculations ($5\times10^7$ pfu) caused a slight growth inhibition of virus-inoculated tumors compared to mock-inoculated tumors ($p=0.08$ at day 10), but no effect on non-inoculated contralateral tumors was observed. This lack of effect on contralateral tumors in athymic mice indicates a T cell component to the elicited immune response.

Tumor-Specific CTL Response

To determine whether the herpes simplex virus induces a tumor-specific CTL response, effector cells were generated in vitro from splenocytes obtained 12 days after the first virus (G207) inoculation and tested in a $^{51}$Cr release assay.

Single-cell suspensions of splenocytes ($3\times10^6$) from individual mice treated with G207 or mock were cultured with $1\times10^6$ mitomycin C-treated CT26 cells (100 μg/ml of mitomycin C for 1 hr). Effector cells were harvested after 6 days of in vitro culturing and mixed with target cells at the ratios indicated. Target cells were incubated with 50 μCi of Na$^{51}$CrO$_4$ ($^{51}$Cr) for 60 min. Four-hour $^{51}$Cr release assays were performed as described in Kojima et al., *Immunity* 1: 357–64 (1994). The % Specific Lysis was calculated from triplicate samples as follows:

[(experimental cpm−spontaneous cpm)/(maximum cpm−spontaneous cpm)]×100.

A20 is a B cell lymphoma cell line (Ig$^+$, Ia$^+$, H-2$^d$) derived from a spontaneous reticulum cell neoplasm in BALB/c mice. Kim et al., *J. Immunol.* 122: 549–54 (1979). It is capable of presenting protein antigen to MHC-restricted antigen-reactive T lymphocytes. Glimcher, et al., *J. Exp. Med.* 155: 445–59 (1982).

Mice treated intratumorally with G207 generated a highly specific CTL response against CT26 cells but not against A20 lymphoma cells (also H-2$^d$). No specific CTL response was detected in mice treated intradermally with G207 or intratumorally with mock extract. There was a small non-specific CTL response (against A20 and CT26) induced in mock-inoculated mice.

The ability of CTL generated in mice inoculated intratumorally with the herpes simplex virus to recognize the CT26 immunodominant MHC-class I restricted antigenic peptide AH1 also was evaluated. AH1, the nonamer SPSYVYHQF (SEQ ID NO: 1), is the immunodominant peptide from CT26, presented by the MHC class I L$^d$ molecule. The L$^d$-binding AH1 peptide is derived from gp70, one of two env gene products of the endogenous MuLV. Huang et al., supra, demonstrated that CT26 cells express the MuLV env gene product while the normal tissues of BALB/c mice do not, and that the viral antigen, gp70, can serve as a potential tumor rejection antigen for the immune system. The AH1 peptide was synthesized by Peptide Technologies (Washington, D.C.) to a purity of >99% as determined by HPLC and amino acid analysis.

H-2L$^d$-restricted P815AB.35-43, LPYLGWLVF (SEQ ID NO: 2), is the immunodominant peptide derived from murine mastocytoma P815 cells. Van den Eynde et al., *J. Exp. Med.* 173: 1373–84 (1991).

Intradermal inoculation with G207 virus or intratumoral inoculation with mock extract did not enhance the activation of specific T cells against CT26 tumors. In contrast, in vivo priming against tumors that express endogenous antigens by intratumoral inoculation of G207 induced an antigenic peptide-specific CTL response. These results indicate that the inoculation of tumors with a herpes simplex virus can overcome potential mechanisms of tolerance to endogenous antigen expression. The lack of an antitumor response against non-inoculated tumors in athymic mice and the loss of CTL activity by depletion of CD8$^+$ cells in vitro suggests an important role for T cell-mediated, MHC class I-restricted recognition by CTL.

Example 2

Antitumor Efficacy of G207 in M3 Mouse Melanoma Cells

M3 mouse melanoma cells ($3\times10^5$) were inoculated bilaterally into the flanks of DBA/2 mice. When the tumors were 5 mm in maximal diameter, the right flank tumor was inoculated one time with either $5\times10^7$ pfu of G207 or an equivalent amount of mock Vero cell preparation (as a negative control).

Figure 2:
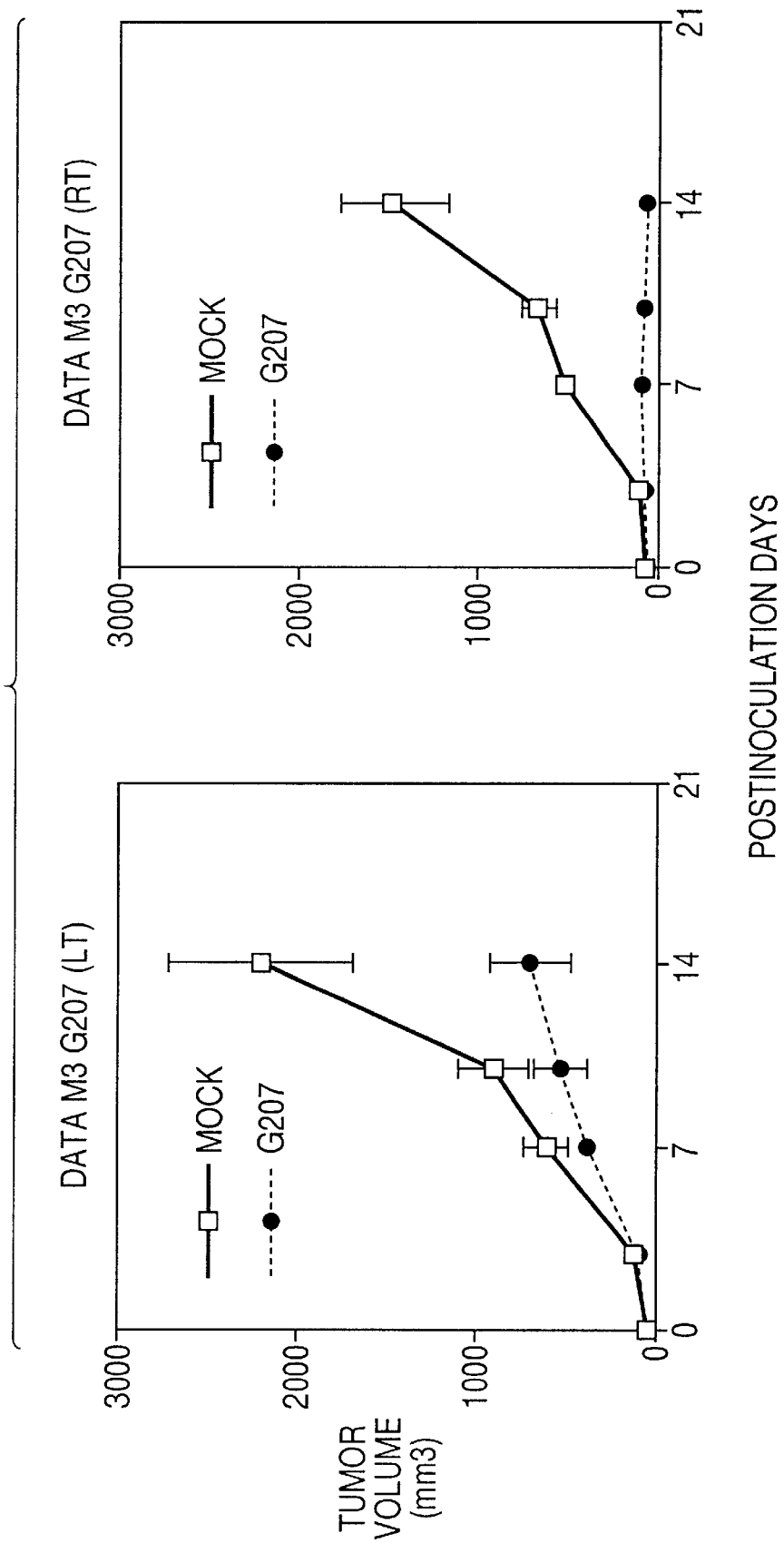
FIG. 2 shows that intratumoral inoculation of M3 mouse melanoma cells in DBA/2 mice with G207 inhibits the growth of the inoculated tumor (rt) and a distant non-inoculated tumor (lt). Bars represent means±SEM of 6 or 7 mice per group. Tumor Volume=(width×length×height).

Inoculation with G207 inhibited the growth of the inoculated tumor ($p<0.0005$), and also significantly inhibited the growth of the non-inoculated tumor ($p<0.02$). FIG. 2.

Example 3

Antitumor Efficacy of G207 in Mouse N18 Neuroblastoma Cells

Bilateral Subcutaneous Tumors

Figure 3:
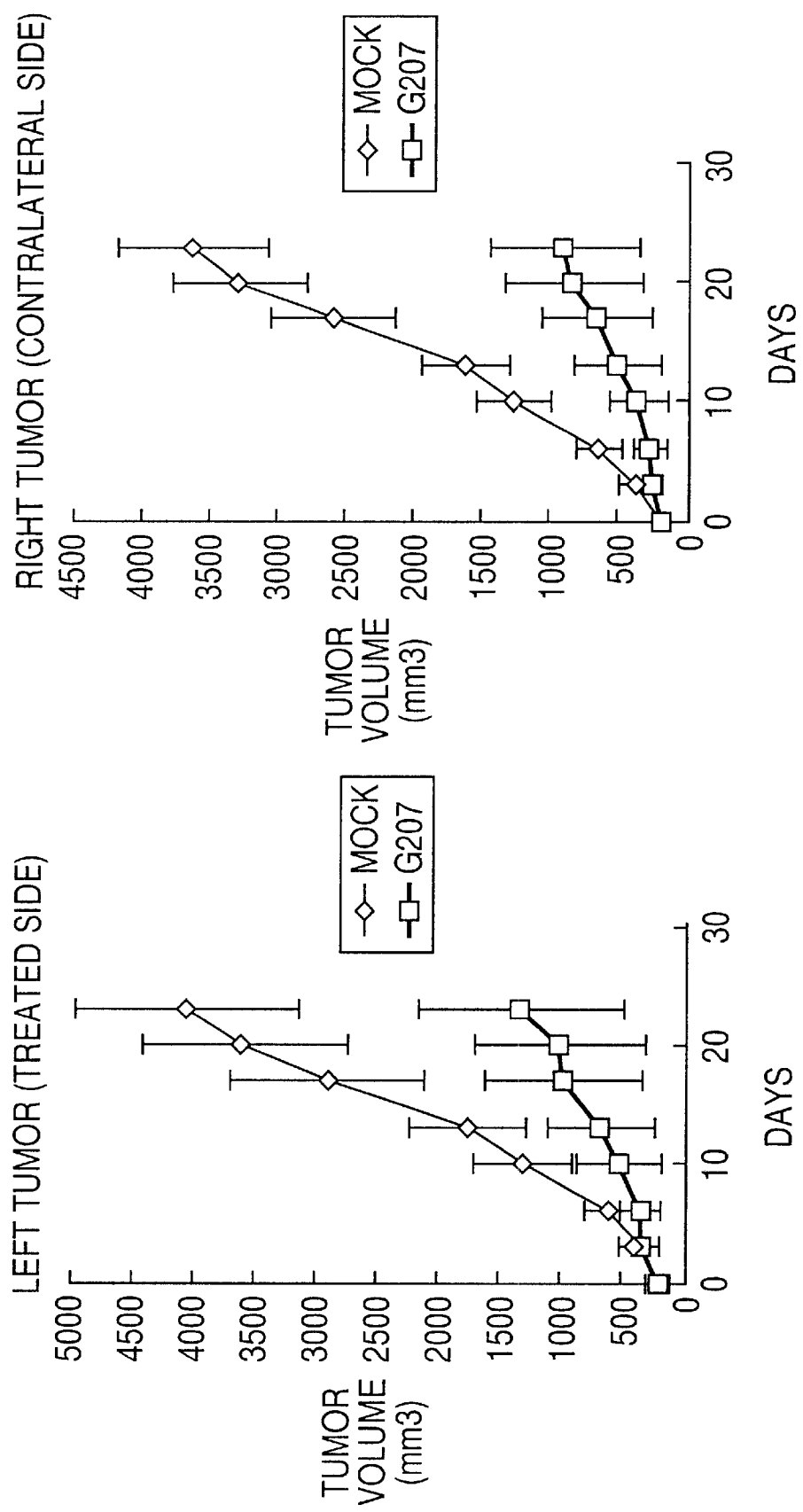
FIG. 3 shows that intratumoral inoculation of mouse N18 neuroblastoma cells in syngeneic A/J mice with G207 inhibits the growth of the inoculated tumor (Left Tumor) and a distant non-inoculated tumor (Right Tumor). Bars represent means±SEM of 8 mice per group. Tumor Volume=(width×length×height).

Mouse N18 neuroblastoma cells were subcutaneously implanted bilaterally into syngeneic A/J mice. Eight days after tumor implantation, $10^7$ pfu of G207 or mock were injected into the left tumor. In six of eight animals, inoculation with G207 resulted in the disappearance of the tumors on both sides. FIG. 3.

Subcutaneous and Intracerebral Tumors

N18 neuroblastoma cells were subcutaneously implanted bilaterally into the left flank of A/J mice. Three days later, N18 neuroblastoma cells were intracerebrally implanted into the right frontal lobe of the mice. on days 10 and 13, the subcutaneous tumors only were injected with G207 (11 mice) or mock (11 mice). Within 35 days of cerebral implantation, all mock-treated mice died-from or had intracerebral tumors. Four out of eleven mice treated with G207 had no intracerebral tumors, and one G207-treated mouse was a long-term survivor. G207 treatment inhibited growth of distant, intracerebral tumors and increased the survival of tumor-bearing animals ($P<0.05$ by Wilcox test).

Rechallenge with N18

Ten A/J mice with no previous exposure to N18 cells (naive group), thirty A/J mice that had spontaneously rejected prior subcutaneous injections of N18 cells (rejection group) and twelve A/J mice that previously had established N18 subcutaneous tumors that were cured by intratumoral injection of G207 (cured group) were subcutaneously injected with N18 cells. None of the animals of the cured group showed any sign of tumor growth, whereas a large number of animals of the naive and rejection groups showed significant tumor growth.

Example 4

Antitumor Efficacy of tsK

Figure 4:
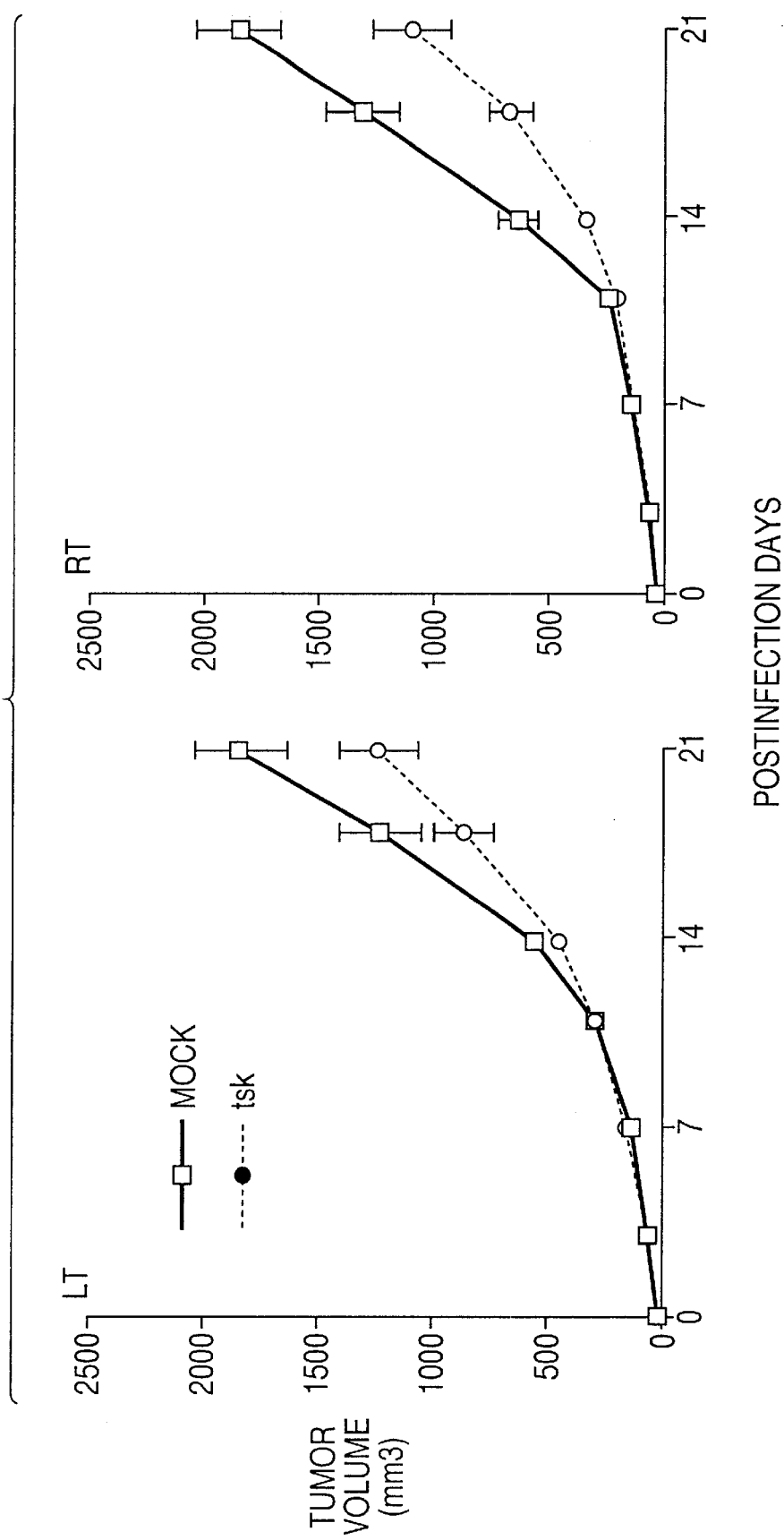
FIG. 4 shows that intratumoral inoculation of CT26 tumors in BALB/c mice with tsK inhibits the growth of the inoculated tumor (Rt) and a distant non-inoculated tumor (Lt). Bars represent means±SEM of 6 mice per group. Tumor Volume=(width×length×height).

Mouse CT26 colon carcinoma cells were subcutaneously implanted bilaterally into syngeneic BALB/c mice. $10^5$ pfu of tsK, a temperature-sensitive herpes simplex virus mutant in ICP4, or mock was injected into the right tumor, and a second inoculation of the same composition was given seven days later (day 7). Inoculation with tsK resulted in significant inhibition of tumor growth in both tumors ($p<0.05$ on day 21). FIG. 4.

Example 5

Antitumor Efficacy of a Defective Vector Containing IL-12 and Helper Virus G207

The murine colorectal carcinoma cell line CT26 was used to evaluate the antitumor efficacy of a defective vector containing IL-12 and G207 as the helper virus.

Generation of Defective Vectors

Figure 5A:
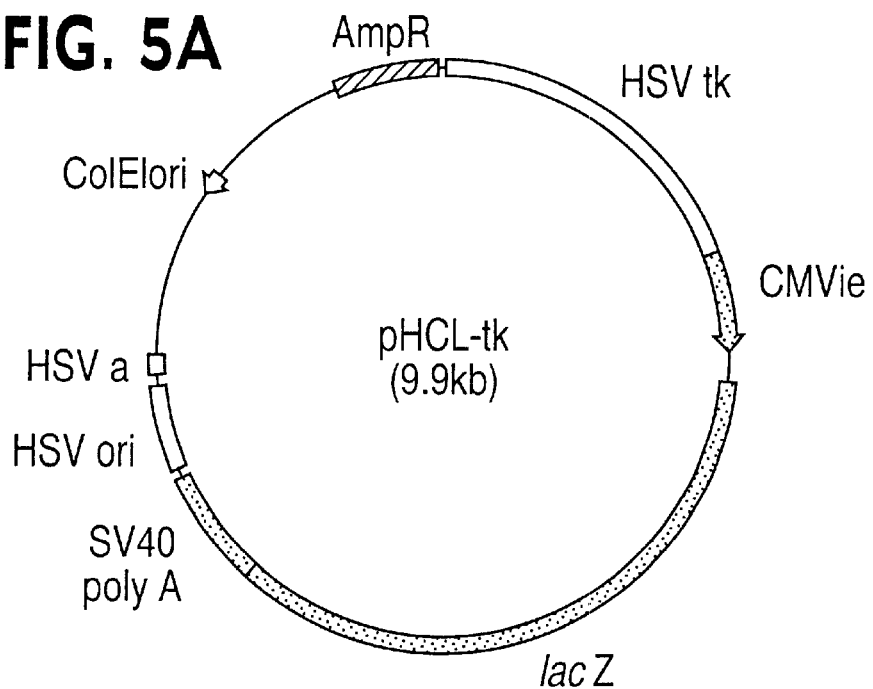
FIG. 5A shows plasmid pHCL-tk.
Figure 5B:
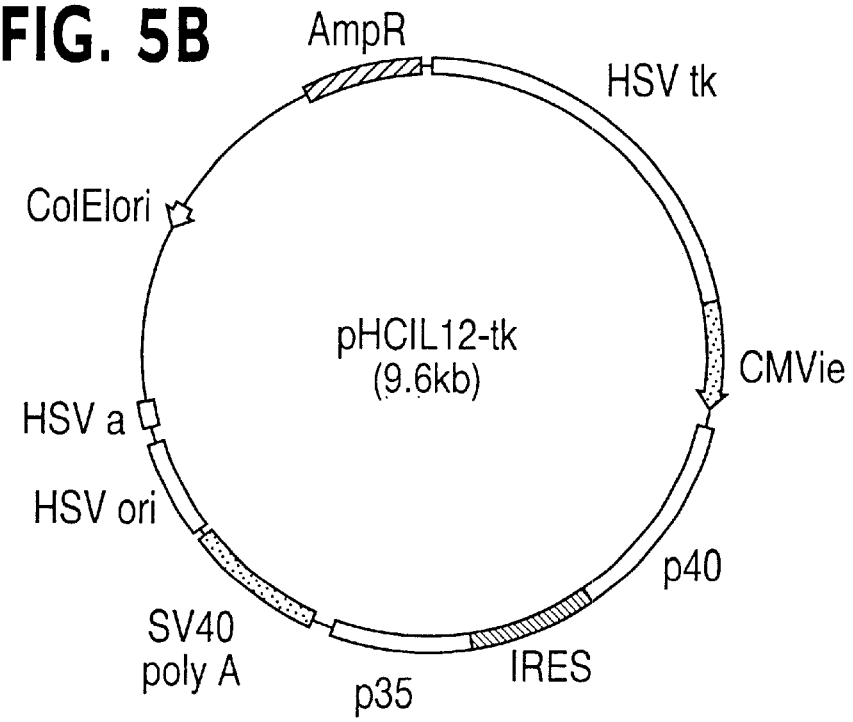
FIG. 5B shows plasmid pHCIL12-tk.

Two amplicon plasmids of similar size were constructed, pHCIL12-tk and pHCL-tk, which encoded the two subunits of murine IL-12 (p40 and p35) or lacZ, respectively, under control of the $CMV_{IE}$ promoter (see FIGS. 5A and 5B). Since IL-12 is functional as a heterodimer, both subunits were expressed from a single defective vector, as a bicistronic message, by means of an internal ribosome entry site (IRES).

The double-cassette amplicon plasmid pHCL-tk was constructed by inserting the HSV-1 thymidine kinase (TK) gene and the blunt-ended BamHl fragment from pHSV-106 (Life Technologies, Inc., Rockville, Md.) into the blunt-ended Spe I site of pHCL (FIG. 5A).

The coding region of p40, BamH1 fragment from BL-pSV40, cDNA for murine IL-12 p35 and an IRES from equine encephalomyocarditis virus (EMCV) from DFG-mIL-12 (IRES-p35), and BamH1 fragment from DFG-mIL12 were subcloned into LITMUS 28 (New England Biolabs, Ma.) at the BglII/BamH1 site to generate p40-IRES-35. The IL-12 encoding double-cassette amplicon plasmid pHCIL12-tk was constructed by insertion of the p40-IRES-p35 cassette, SnaB1/AflII fragment, into the blunt-ended SalI site of pSR-ori and then inserting the HSV TK blunt-ended BamH1 fragment into the blunt-ended SphI site to produce pHCIL12-tk. FIG. 5B.

G207, containing deletions in both copies of the γ34.5 gene and an *E. coli* lac Z insertion inactivating the ICP6 gene, was used as helper virus for the generation of defective vector (dv) stocks. Vero cells were co-transfected with purified amplicon plasmid DNA (pHCIL12-tk and pHCL-tk) and G207 viral DNA using lipofectAMINE™ (Life Technologies, Inc., Rockville, Md.), as described by the manufacturer, and then cultured at 34.5° C. until they exhibited complete cytopathic effect. Virus was then harvested and passaged at a 1:4 dilution in Vero cells until inhibition of helper virus replication was observed. The IL-12 containing defective vector is called dvIL12/G207 and the lacZ containing defective vector is called dvlacZ/G207.

Titering of Defective Vector Stocks

Defective vector stocks were titered after a freeze-thaw/sonication regime and removal of cell debris by low-speed centrifugation (2000×g for 10 min at 4° C.). G207 helper virus titer was expressed as the number of pfus after plaque assay on Vero cells at 34.5° C. For dvIL12/G207, IL-12 expression was determined and the passage with highest level was used (passage 4) with a G207 helper virus titer of $5\times10^7$ pfu/ml. The titer of dvlacZ/G207, determined by counting X-gal (5-bromo-4-chloro-3-indolyl-β-D-glactopyranoside) histochemistry positive single cells (defective particle units, dpu) after formation of plaques by G207, was $5\times10^6$ dpu/ml and $5\times10^7$ pfu/ml of helper virus.

Cell Culture

African green monkey kidney (Vero) cells were cultured in DMEM containing 10% calf serum (CS). MC-38 mouse colon adenocarcinoma, Harding-Passey mouse melanoma, MDA-MB-435 human breast adenocarcinoma, and CT26 cells were grown in DMEM containing 10% heat-inactivated FCS (Hyclone, Logan, Utah) and penicillin-streptomycin (Sigma Chemical Co, St Louis, Mo.) A20, a B cell lymphoma cell line ($Ig^+$, $Ia^+$, $H-2^d$) derived from a spontaneous reticulum cell neoplasm in BALB/c mice (American Type Culture Collection, Rockville, Md., ATCC TIB 208) was grown in RPMI 1640 containing 10% heat-inactivated FCS, 50 μM of 2-ME, 2 mM glutamine, 20 mM Hepes buffer, and penicillin-streptomycin.

Detection of IL-12

The expression and secretion of IL-12 was determined by ELISA assay after infection of tumor cells in culture at a multiplicity of infection (MOI) of 1 pfu per cell.

24 hours post-infection, aliquots of infected cell supernatant were removed, quick frozen in a dry-ice/ethanol bath, and stored at −80° C. for detection of IL-12. Tumors and blood were collected from defective vector-treated mice and snap-frozen in a dry-ice/ethanol bath. Frozen tissue was homogenized in ice-cold PBS containing 500 μM PMSF, 0.5 μg/ml leupeptin and 0.7 μg/ml pepstatin. The homogenate was then sonicated twice for 10 seconds and cleared by centrifugation in a microfuge for 5 min at 4° C. Immunoreactive IL-12 levels were determined by sandwich ELISA, using Ab pairs and rIL-12. The rIL-12 standards were diluted in the same media or buffer as the samples (i.e., mouse serum for the serum samples).

Briefly, 96-well plates coated with an anti-mouse IL-12 mAb (9A5) were incubated overnight at room temperature with the test samples. After washes, the plates were incubated with peroxidase-labelled anti-mouse IL-12 p40 Ab (5C3) for 2 hours and then were developed. Absorbance was measured at 450 nm.

Figure 6:
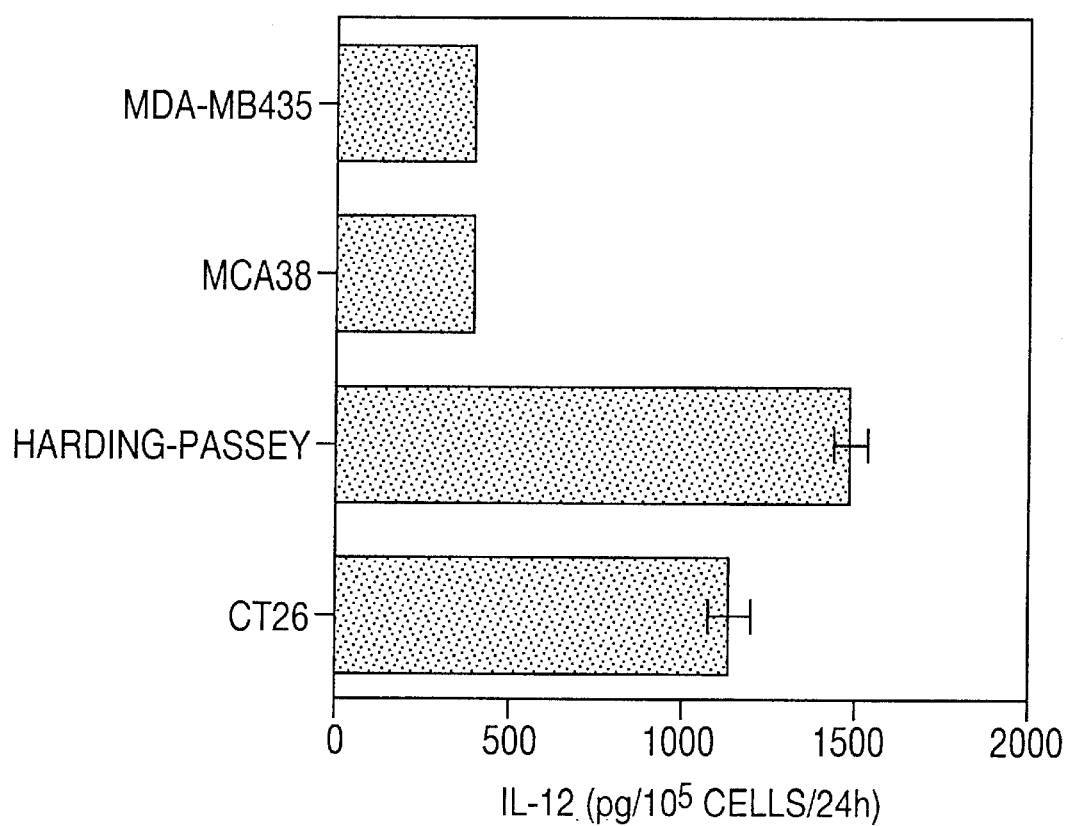
FIG. 6 shows the secretion of IL-12 in cells inoculated with dvIL12/G207.

Infection of CT26 (murine colon carcinoma), Harding-Passey (murine melanoma), MCA38 (murine colon adenocarcinoma) and MDA-MB-435 (human breast adenocarcinoma) cells with dvIL12/G207 resulted in secretion of up to 1.5 ng murine IL-12/$10^5$ tumor cells in 24 hours. FIG. 6. No IL-12 was detected in the supernatants of uninfected tumor cell cultures or those infected with dvlacZ/G207. Levels of IL-12 synthesis and secretion peaked 1 day after dvIL12/G207 infection of CT26 cells and decreased to undetectable levels by 3 days post-infection, likely due to cell death.

Subcutaneous Tumor Model

BALB/c and BALB/c (nu/nu) mice were obtained from the National Cancer Institute or Charles River (Wilmington, Ma.). All animal procedures were approved by the Georgetown University Animal Care and Use Committee.

CT26 tumor cells ($1\times10^5$) were injected subcutaneously (s.c.) in the bilateral flanks of mice. When s.c. tumors were palpably growing (approximately 5 mm in maximal diameter), mice were unilaterally inoculated into the right side tumor with either 50 μl of defective HSV vector (7×10$^5$ pfu of helper virus) in virus buffer (150 mM NaCl, 20 mM Tris, pH 7.5) or 50 μl virus buffer, followed by a second injection of the same composition 7 days later. Where indicated, mock extract was used in place of virus buffer. DvlacZ/G207 rather than helper virus G207 alone was used as a control for dvIL12/G207 inoculation so that differences in viral factors (i.e., particle:pfu ratio) present in defective vector stocks versus G207 stocks would be accounted for. Both G207 and dvlacZ contain *E.coli* lacZ and therefore no additional foreign antigens were expressed by the control defective vector.

Tumor size was measured by external caliper and tumor volume was calculated (V=h×w×d). If animals appeared moribund or the diameter of their s.c. tumors reached 18 mm, they were sacrificed and this was recorded as the date of death for survival studies. Statistical differences were calculated using StatView 4.5 (Abacus Concepts Inc., Berkeley, Calif.) where mean tumor volume was assessed by unpaired t-test, survival means by ANOVA (Fisher's post-hoc comparisons) and differences in survival by Logrank (Mantel-Cox) test.

Figure 7:
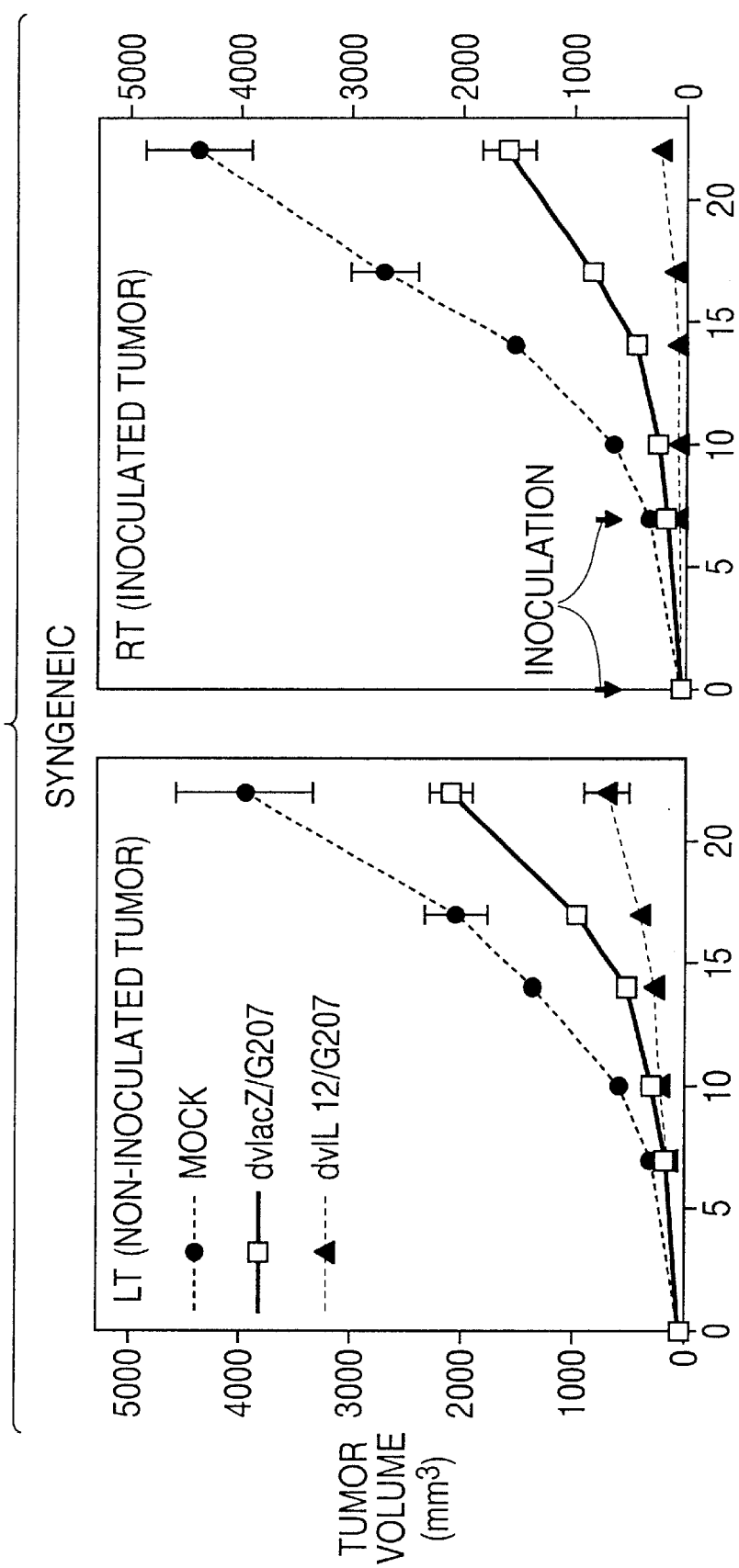
FIG. 7 shows that intratumoral inoculation of CT26 tumors in BALB/c mice with dvlacZ/G207 or dvIL12/G207 inhibits the growth of the inoculated tumor (Rt) and a distant non-inoculated tumor (Lt). Bars represent means±SEM of 6 mice per group. Tumor Volume=(width×length×height).

Inoculation with dvIL12/G207 elicited a very prominent antitumor effect, with both the inoculated tumors as well as their non-inoculated contralateral counterparts demonstrating a significant reduction in tumor growth. FIG. 7. Two out of six of the dvIL12/G207 inoculated tumors regressed to an undetectable size. Inoculation with dvlacZ/G207 also resulted in a significant reduction in tumor growth of both inoculated and non-inoculated tumors compared to controls, although to a much lesser extent than dvIL12/G207. FIG. 7.

Figure 8:
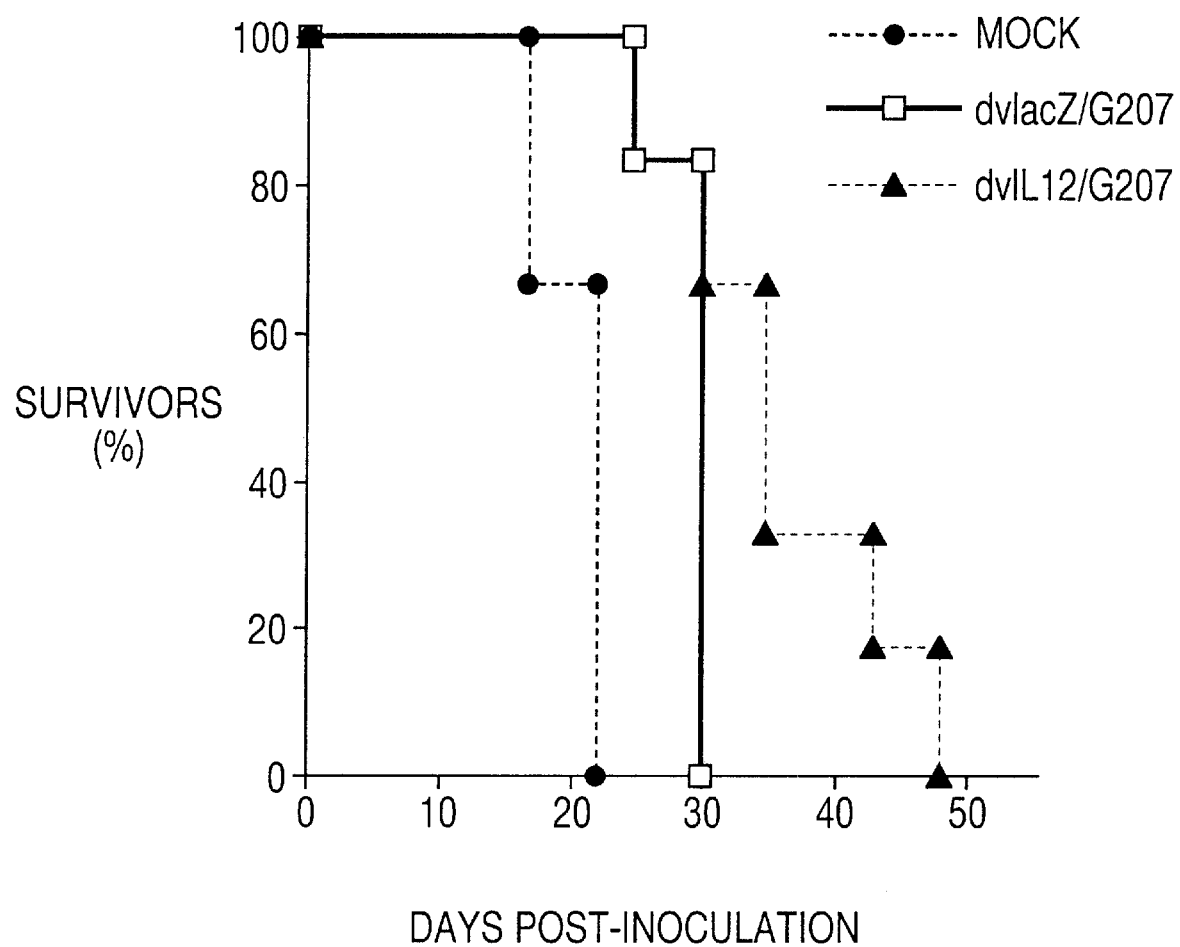
FIG. 8 shows the survival rate of mice post-inoculation with dvlacZ/G207, dvIL12/G207 or mock.

Mice also were followed for survival, where sacrifice occurred when either of the bilateral tumors became larger than 18 mm in diameter. Survival of the defective vector-treated animals is therefore reflective of the growth of the non-inoculated tumors and was significantly longer than control animals. Mice treated unilaterally with dvIL12/G207 survived longer than dvlacZ/G207 treated mice (FIG. 8). IL-12 was detected in the dvIL12/G207 inoculated tumors one and five days post-inoculation (approximately 50–100 pg/tumor), with no IL-12 detected in the serum.

Role of T Cells in Immune Response

To evaluate the possible role of T cells in the defective HSV vector-induced antitumor response, bilateral CT26 s.c. tumors were established in athymic BALB/c (nu/nu) mice. As with the immune-competent murine model discussed above, unilateral intratumoral inoculation of dvIL12/G207, dvlacZ/G207 or mock-extract was performed into the right side tumors when they were palpable (approximately 5 mm in maximal diameter), and a second inoculation of the same composition was given seven days later.

Although there was a slight delay in growth of right side tumors injected with dvIL12/G207, no significant tumor growth inhibition was observed in either the inoculated or contralateral non-inoculated tumors. CT26 tumors grew somewhat more rapidly in the athymic mice than in the immune-competent mice.

Tumor-specific CTL response

To test whether inhibition of tumor growth was associated with increased CTL activity, the ability of intratumoral inoculation with defective HSV vectors to elicit CT26-specific CTL activity in vitro was examined using a $^{51}$Cr release assay.

BALB/c mice were inoculated with dvIL12/G207 or dvlacZ/G207 intratumorally when s.c. tumors reached approximately 5 mm in maximal diameter, and a second inoculation of the same composition was given seven days later. Single-cell suspensions of splenocytes were cultured in RPMI 1640 medium with 10% inactivated FCS, 50 μM 2-ME, 2 mM glutamine, 20 mM Hepes, and penicillin-streptomycin in 24-well plates at a concentration of 3×10$^6$ cells/ml. In addition, either 1×10$^6$ inactivated CT26 cells or 1 μg/ml of peptide AH1 was added to the medium. For inactivation, CT26 tumor cells were incubated for 1 hour in culture medium containing 100 μg/ml of mitomycin C and then washed 2 times. Effector cells were harvested after 6 days of in vitro culture.

Four-hour $^{51}$Cr release assays were performed as described above. In brief, target cells were incubated with 50 μCi of Na$^{51}$CrO$_4$ ($^{51}$Cr) for 60 min. A20 cells were pulsed with 1 μg/ml of the L$^d$-restricted peptides AH1 or P815AB for 1 h before labeling. Target cells were then mixed with effector cells for 4 h at the E/T ratios indicated. The amount of $^{51}$Cr release was determined by 7 counting, and the percent specific lysis was calculated from triplicate samples as follows:

[(experimental cpm−spontaneous cpm)/(maximum cpm−spontaneous cpm)]×100.

Effector cells from dvIL12/G207 treated mice restimulated with mitomycin-C treated CT26 cells exhibited specific lysis of CT26 target cells and of A20 cells pulsed with peptide AH1. No apparent lysis of unpulsed A20 cells or A20 cells pulsed with L$^d$-restricted peptide P815AB was observed. Effector cells restimulated with peptide AH1 from mice treated with dvIL12/G207 or dvlacZ/G207 exhibited specific lysis of target A20 cells pulsed with peptide AH1 and of CT26 cells, but not of unpulsed A20 cells. The level of CTL activity generated by dvIL12/G207 was significantly greater than that generated by dvlacZ/G207. Effector cells from dvIL12/G207 inoculated animals, not restimulated, were able to specifically lyse CT26 but not A20 cells.

The effect of intratumoral IL-12 expression on the accumulation of particular T lymphocyte subtypes or IFN-γ production also was determined. Splenocytes were isolated five days after the second inoculation of dvIL12/G207 or dvlacZ/G207 and tested for IFN-γ production by ELISA and splenic T lymphocyte subsets by FACS analysis. Briefly, single-cell suspensions of splenocytes were washed and resuspended in RPMI 1640 medium containing 10% inactivated FCS. Cells (3×10$^6$/ml) were cultured in 24-well plates for 24 h. Supernatants were collected and assayed by a sandwich ELISA using anti-IFN-γ Ab pairs obtained from Endogen (Woburn, Ma.).

Similar percentages of a helper T cells (CD4) and a cytotoxic T cells (CD8a) were found in dvIL12/G207 and dvlacZ/G207 treated mice. Splenocytes from mice treated with dvIL12/G207 produced significantly greater amounts of IFN-γ than those treated with dvlacZ/G207, as shown below.

| Treatment | IFN-γ (ng/ml) |
|---|---|
| dvIL12 | 16 ± 6 |
| dvlacZ | 1.6 ± 0.6 |

Example 6

Antitumor Efficacy of a Vector Containing tsK and IL-12

Defective vectors containing IL-12 and tsK or lacZ and tsK were prepared. Defective vector plasmids pHCIL12-tk and pHCL-tk were prepared as described above. Defective vectors were generated by co-transfection of Vero cells with helper virus tsK DNA and pHCIL12-tk or pHCL-tk. Transfected cells were incubated at 31.5° C. (a replication-permissive temperature for tsK) until total cytopathic effect was observed. The cells then were passaged as described above for G207 helper virus. See also Kaplitt et al., *Mol. Cell. Neurosci.* 2: 320–30 (1991). The defective vector containing IL-12 is called dvIL12/tsK and the defective vector containing lacZ is called dvlacZ/tsK.

Figure 9:
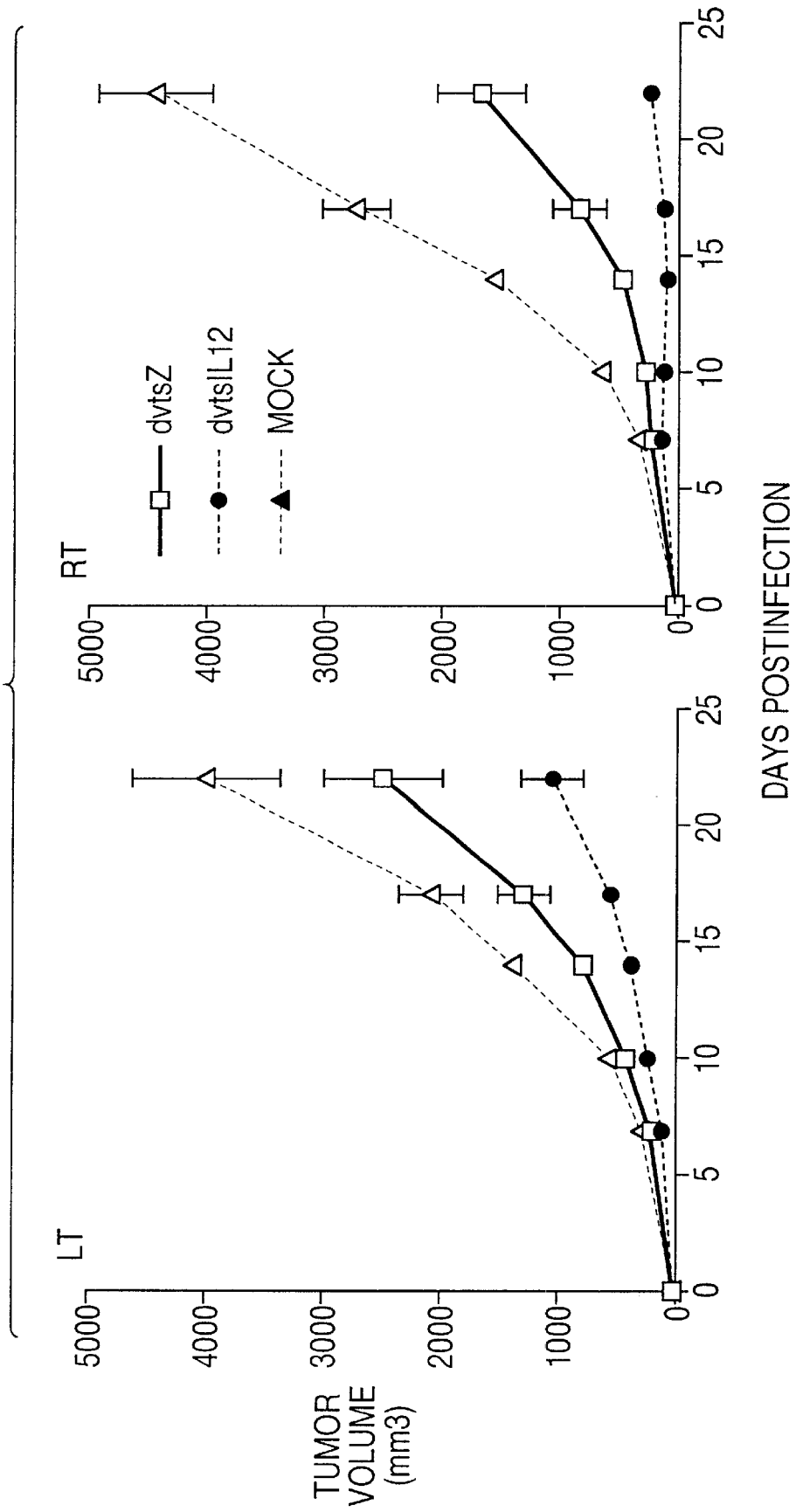
FIG. 9 shows that inoculation of CT26 tumors in BALB/c mice with dvIL12/tsK or dvlacZ/tsK inhibits the growth of the inoculated tumor (Rt) and a distant non-inoculated tumor (Lt). Bars represent means±SEM of 6 mice per group. Tumor Volume=(width×length×height).

CT26 mouse colon carcinoma cells were subcutaneously implanted bilaterally into syngeneic BALB/c mice, as described above. The right tumor was inoculated with either dvlacZ/tsK, dvIL12/tsK or mock, and a second inoculation of the same composition was given seven days later. Inoculation with dvlacZ/tsK resulted in a significant inhibition of tumor growth in both tumors ($p<0.01$ on day 22). Inoculation with dvIL12/tsK resulted in greater inhibition of tumor growth in both tumors compared to dvlacZ/tsK-inoculated tumor ($p<0.001$). FIG. 9.

GM-CSF cDNA in place of IL-12 DNA; expression of GM-CSF was detected by ELISA) and helper tsK virus, or with virus buffer. Mice treated with dvGMCSF/tsK showed increased survival over mice treated with dvlacZ/tsk or buffer, and showed decreased tumor growth in both bilateral tumors.

It is to be understood that the description, specific examples and data, while indicating exemplary embodiments, are given by way of illustration and are not intended to limit the present invention. Various changes and modifications within the present invention will become apparent to the skilled artisan from the discussion, disclosure and data contained herein, and thus are considered part of the invention.

SEQUENCE LISTING

```
<160> NUMBER OF SEQ ID NOS: 2

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 1

Ser Pro Ser Tyr Val Tyr His Gln Phe
1               5

<210> SEQ ID NO 2
<211> LENGTH: 9
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 2

Leu Pro Tyr Leu Gly Trp Leu Val Phe
1               5
```

Figure 10:
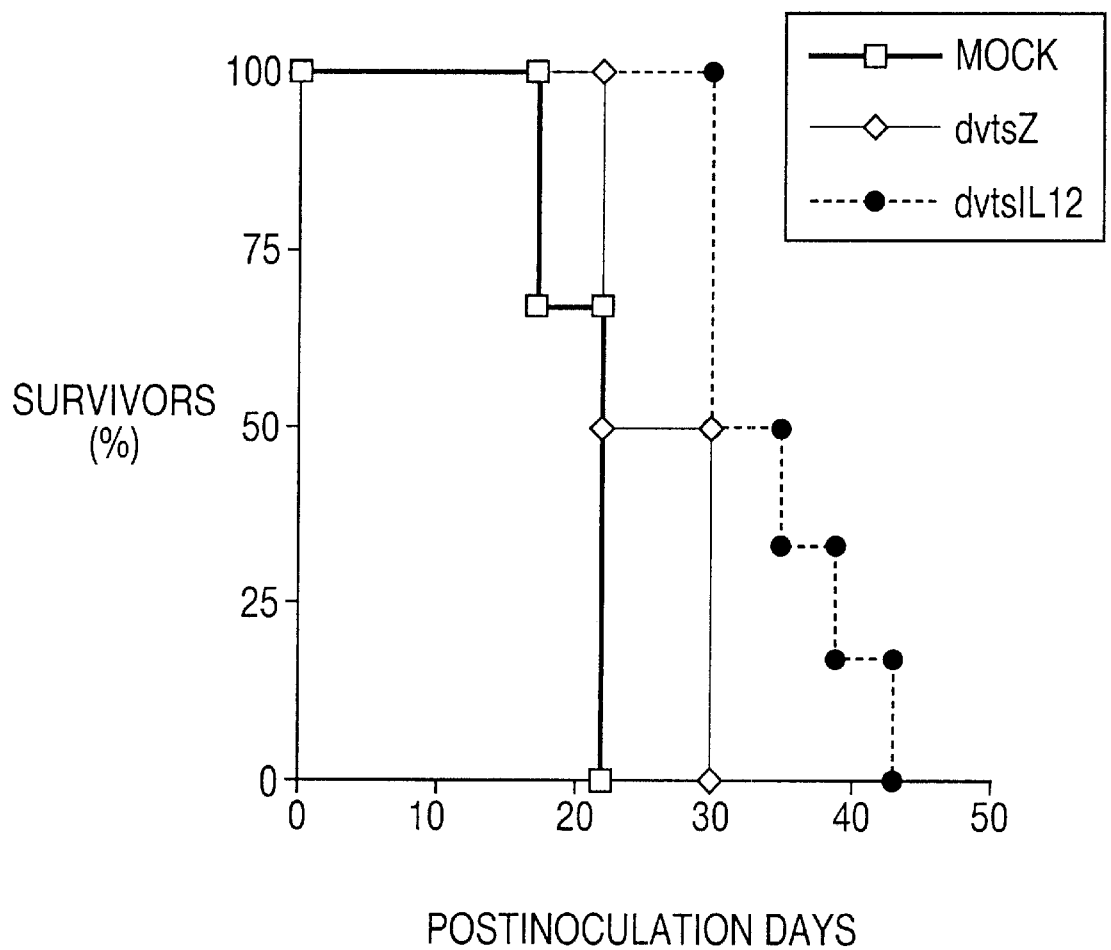
FIG. 10 shows the survival rate of mice post-inoculation with dvlacZ/tsK, dvIL12/tsK or mock.

The survival of inoculated mice also was followed. Mice were sacrificed when they became moribund or when their tumors reached greater than 18 mm in diameter. As shown in FIG. 10, mice inoculated with dvlacz survived significantly longer than mice inoculated with mock ($p<0.01$), and mice inoculated with dvIL12/tsK survived significantly longer than mice inoculated with dvlac/tsK or mock ($p<0.01$).

Example 7

Antitumor Efficacy of a Vector Containing tsK and GMCSF

Harding-Passey melanoma cells were subcutaneously implanted into the bilateral flanks of C57BL/6 mice. When the tumors were about 5 mm in maximal diameter (day 0), the right flank tumors were injected with defective vector dvlacZ/tsk (generated from the amplicon plasmid pHCL-tk and expressing *E. coli* lacZ) or dvGMCSF/tsK (generated from the amplicon plasmid pHCGMCSF-tk, whose structure is the same as pHCIL12-tk except it contains mouse

What is claimed is:

1. A method of eliciting a systemic antitumor immune response in a patient who presents with or who is at risk of developing multiple metastatic tumors of a given cell type, comprising the step of inoculating a tumor in the patient with a pharmaceutical composition consisting essentially of:

(A) a member selected from the group consisting of (i) HSV type 1 mutant G207, (ii) HSV type 1 mutant tsk, (iii) a combination of helper HSV G207 or tsk and a defective HSV derived from G207 or tsk comprising an HSV amplicon encoding the marker gene LacZ under the operative control of transcriptional regulatory elements, and (iv) a combination of helper HSV G207 or tsk and a defective HSV derived from G207 or tsk comprising an HSV amplicon encoding Interleukin-12 under operative control of transcriptional regulatory elements, and (B) a pharmaceutically acceptable vehicle for the virus, such that an immune response is induced that is specific for the tumor cell type and that kills cells of the inoculated tumor and of a non-inoculated tumor.

2. The method of claim 1, wherein the pharmaceutical composition comprises the mutant G207.

3. The method of claim 1, wherein the pharmaceutical composition comprises the ICP4 mutant tsk.

4. The method of claim 1, wherein the tumor cells are of a type selected from the group consisting of astrocytoma, oligodendroglioma, meningioma, neurofibroma, glioblastoma, ependymoma, Schwannoma, neurofibrosarcoma, and medulloblastoma.

5. The method of claim 1, wherein the tumor cells are selected from the group consisting of melanoma cells, pancreatic cancer cells, prostate carcinoma cells, head and neck cancer cells, breast cancer cells, lung cancer cells, colon cancer cells, lymphoma cells, ovarian cancer cells, renal cancer cells, neuroblastomas, squamous cell carcinomas, medulloblastomas, hepatoma cells and mesothelioma and epidermoid carcinoma cells.

6. The method of claim 1, wherein the patient presents with multiple metastatic tumors.

7. The method of claim 1, wherein the pharmaceutical composition comprises a combination of helper HSV G207 or tsk and a defective HSV derived from G207 or tsk comprising an HSV amplicon encoding the marker gene LacZ under the operative control of transcriptional regulatory elements.

8. The method of claim 1, wherein the pharmaceutical composition comprises a combination of helper HSV G207 or tsk and a defective HSV derived from G207 or tsk comprising an HSV amplicon encoding Interleukin-12 under operative control of transcriptional regulatory elements.

* * * * *